Figure 3:
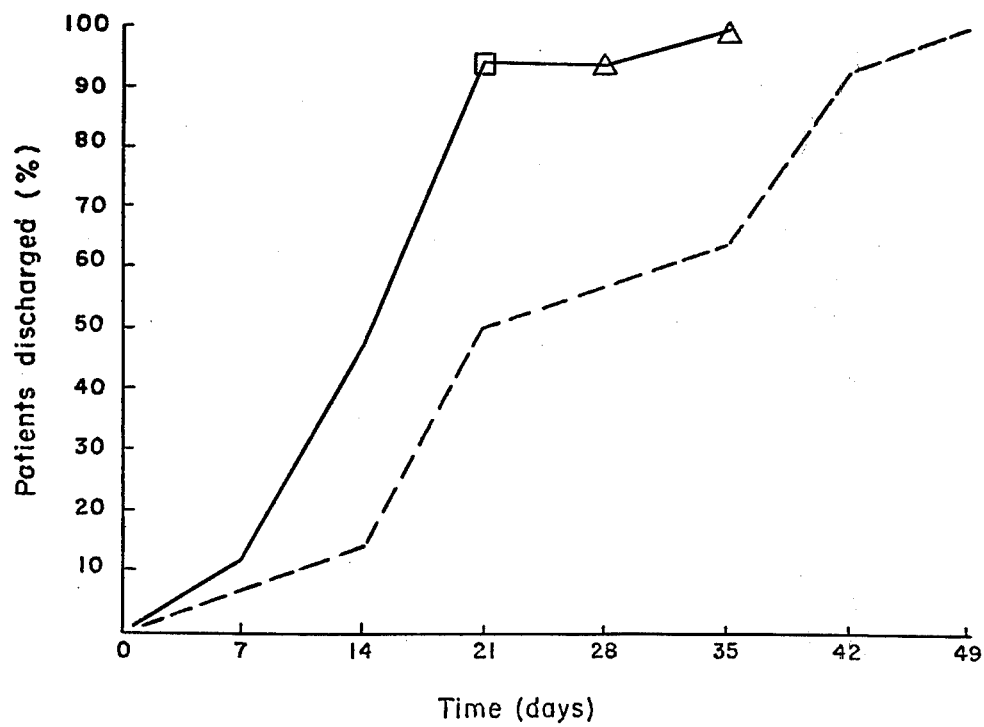

United States Patent [19]

Silvestrini

[11] 4,154,832
[45] May 15, 1979

[54] NOVEL TREATMENT FOR ACUTE ORGANIC CEREBRAL SYNDROMES (STROKES)

[76] Inventor: Bruno Silvestrini, Via Michelangelo Schipa 15, Rome, Italy, 00179

[21] Appl. No.: 748,421

[22] Filed: Dec. 8, 1976

Related U.S. Application Data

[63] Continuation of Ser. No. 608,690, Aug. 28, 1975, abandoned, which is a continuation-in-part of Ser. No. 608,011, Aug. 26, 1975, abandoned.

[30] Foreign Application Priority Data

Aug. 26, 1974 [IT] Italy .............................. 26590 A/74

[51] Int. Cl.² ......................................... A61K 31/495
[52] U.S. Cl. .................................................. 424/250
[58] Field of Search .......................... 424/250; 608/690

[56] References Cited

U.S. PATENT DOCUMENTS 3,381,009  4/1968  Palazzo et al. ...................... 424/250

OTHER PUBLICATIONS

*The Merck Manual,* (1972), 12th Ed., pp. 1320-1329.
*Manual of Medical Therapeutics,* 19th Ed., Smith, Little, Brown and Company, Boston, pp. 355-356.
*Stroke,* vol. 2, Jul.-Aug., 1971, pp. 327 and 341.
*Neurology,* vol. 22, Apr., 1972, pp. 377-383.
Trazodone, Med. Probl., Pharmacopsychiat., vol. 9, Biochemistry Session, Garattini, pp. 29-46, 1974.
*Current Therapy,* (1975), pp. 638-664, W. B. Saunders Co., Phila.
Goodman et al.—(The Pharm. Basis of Ther.)—5th Ed., pp. 721, 722, 740 and 741.

Primary Examiner—Frederick E. Waddell
Attorney, Agent, or Firm—Ladas, Parry, Von Gehr, Goldsmith & Deschamps

[57] ABSTRACT s-Triazolo-[4,3-a]-pyridine derivatives and their non-toxic salts have been found to have pharmaceutical activity in the treatment of individuals suffering from the acute phases of the organic cerebral syndrome (stroke).

1 Claim, 3 Drawing Figures

FIG. 1 Decrease in CSF pressure of rats after single i.v. injection of trazodone. (10 animal replicate)
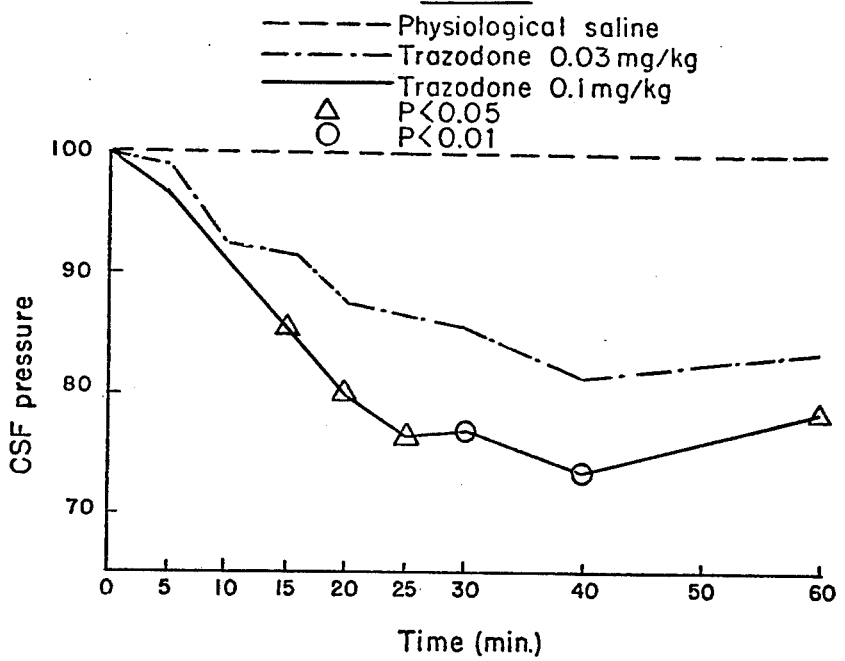
FIG. 2 Average total disability score in treated and control patients.
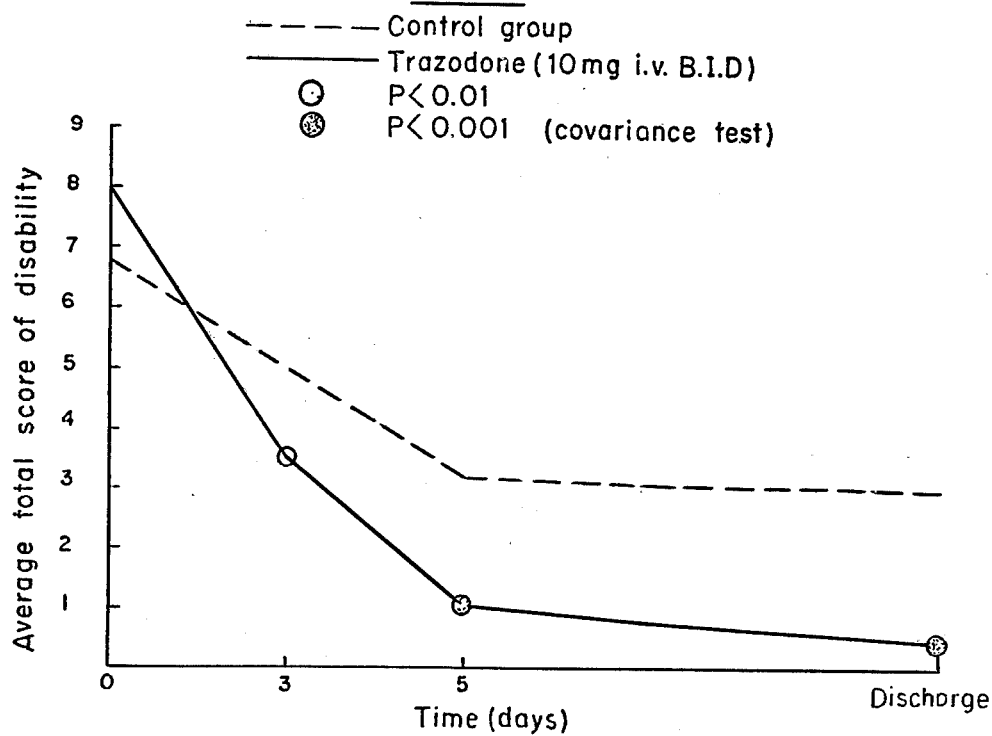

Duration of hospitalization in treated and control patients.
(The percentage of patients discharged at varying times is given.)

NOVEL TREATMENT FOR ACUTE ORGANIC CEREBRAL SYNDROMES (STROKES)

This is a continuation, of application Ser. No. 608,690 filed Aug. 28, 1975, now abandoned, which is a continuation-in-part of U.S. Ser. No. 608,011 filed Aug. 26, 1975, abandoned in favor of U.S. Ser. No. 608,690.

This invention relates to a novel therapeutic treatment for acute organic cerebral syndrome (strokes) by the administration of "Trazodone" the W.H.O. approved generic name for 2,3,4(m-chlorphemyl)-1-piperazinyl-propyl-s-triazolo, 4,3a pyridin-3(2H)one and its related compounds. The compounds are described in U.S. Pat. No. 3,381,009 assigned to the same assignee of the present patent application.

The compounds of U.S. Pat. No. 3,381,009 are derivatives of s-trizolo-[4,3a]-pyridine having the formula:

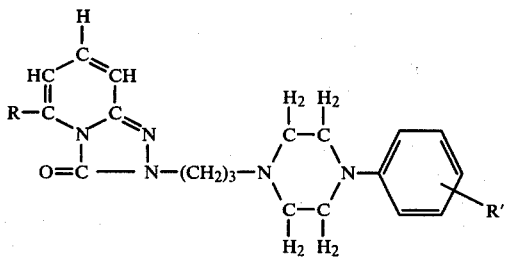

where
R is hydrogen or methyl,
R' is hydrogen, or halogen or
alkyl of 1 to 4 carbon atoms,
alkoxy of 1 to 4 carbon atoms,
and non-toxic salts of these derivatives. The compounds were noted to have tranquilizing and hypotensive activity. The synthesis of the compounds is described in said U.S. Pat. No. 3,381,009. Trazodone, has been accepted internationally as a potent and safe psychopharmacological agent. (Trazone: Proc. First Int. Sym, Montreal 1973: Eds. Th. A. Ban, B. Silverstrini, Modern Problems of Pharmacopsychiatry Vol. 9 Karger, Basle 1974). The other compounds of U.S. Pat. No. 3,381,009 have this same activity but to a lesser degree and have not been commercialized.

In the above mentioned patent, particularly tranquilizing action, hypotensive action and analagesic action have been shown as pharmacological and therapeutic activities of Trazodone. Trazodone has been widely used in therapy as a psycho-active drug. Clinical researches, involving Trazodone have been recently reported at international meetings (Amsterdam, 1973; Montreal, 1973; Buenos Aires, 1974). These reports have specified the major usage of Trazodone in psychoneurosis with symptons of depression; psychosomatic medicine; psychogeriatrics and for depressions of exogenic and endogenic character. The therapeutic effects of Trazodone are related to an extraordinarily selective interference with the troubles of the so-called "experience emotive-affective integration system" (Int. J. Neuropharmacol. 7, 587–599; Silvestrini and Quadri, Europ. J. Pharmacol. 12, 231, 1970; Silvestrini and Lisciani, Curr. Ther. Res 15, 749, 1973). The effects shown by Trazodone are of humoral character and mainly involve an interference with the serotoninergic system (Silvestrini and Quadri (ibid) 1973; Angelucci and Bolle, 1974; Garattini 1974). (See "Trazodone" Proceedings of First International Symposium, Montreal 1973; Eds. Th. A. Ban, B. Silvestrini, Modern Problems of Pharmacopsychiatry Vol 9 Karger, Basle 1974).

A series of observations have suggested that Trazodone could be used in fields other than psychopharmacology. It was observed that Trazodone reduces the intraocular pressure, both in animal (Burberi Arzncimittel-Forsch. 20: 1143–1147, 1970;) and in human being (Daniele and Fiore, Ann. Ottal., 9S: 1–6, 1972). The close physiological correlations between this effect and that of humoral pressure suggested extrapolation of the data not only to the glaucomatous type of pathology, but also to the cerebral syndromes associated with hypertension of the cerebral humor or edema. The potent selective inhibiting action of Trazodone in connection with the peripheral effects of serotonine was also noted. Thus, unlike noradrenalin and adrenalin, Trazodone exerts an action on cerebral arteries in human beings and animals. (Carpri A.: "International Encyclopedia of Pharmacology and Therapeutics" Section 33: 1 155, Pergamon Press, Oxford, 1972.) This effect is more evident in patients suffering from chronic cerebropathias of a vascular basis. It appears that spasms of arteries surrounding focuses of subarachnoid hermorrahage are linkable with a local release of serotonine. It is also generally recognized that the outcome of acute cerebral vasculopathis not only depend on the mechanical obstruction of the vessels, but also on the vasomotor responses of reflected or humoral character being collaterally set up and which might give rise to focuses of cerebromalacia as a result of anoxia.

On the ground of the above indications, the applicant commenced an experimental test program to reproduce acute cerebral lesions in animals and to examine the effects of Trazodone thereon. Particularly, acute neurologic phenomena have been produced in the rat by injecting air into one of the two carotid arteries. Thus, a hemiplegic type of syndrome of sufficient constancy was obtained for accomplishing pharmacological testing. The use of Trazodone at the dose of 1 mg/kg i.v. shown to be capable of substantially reducing the gravity in the above mentioned syndrome as induced in rats, and also reducing the time for recovery.

EXAMPLE 1—Clinical Tests in Human Beings

Tests have been carried out on patients suffering from acute cerebral syndromes, prevailing on hemorrahgic base, equally characterized by hemiplegia. Particularly, the drug was administered to six, over sixty-year-old, patients showing clear symptoms of focus-type of acute vascular disease. The administrations were effected at a dose of 10 mg. Trazodone twice a day, particularly by slow intravenous administration. Besides receiving the Trazodone, the patients were subjected to oxygen-therapy and control of the hydroelectrolytic and caloric balance. The results obtained are summarized in Table I.

Table I

| Age and sex | TRAZODONE PROGRAM ||| 
| | Neurologic clinical exam |||
| | Entry | 5th day | Discharge |
| --- | --- | --- | --- |
| 67 M | Sensory aphasia | Disappearance of aphasia. | |

Table I-continued

TRAZODONE PROGRAM

| Age and sex | Neurologic clinical exam | | |
|---|---|---|---|
| | Entry | 5th day | Discharge |
| | | Slight dysarthria. Retroactive amnesia. | Recovery |
| 68 M | | Total regression. | Recovery |
| 65 F | | Functional autonomy revivial. Slight adiadochocinesia. | Recovery |
| 77 M | Right hemiparesis | Total regression. | Recovery |
| 79 M | Right hemiplegia | Right hemiparesis. | Recovery |
| 71 M | Left hemiparesis | Slight monoparesis. lower extremity | Complete functional autonomy |

By way of comparison, 12 clinical sheets were checked, against random selected encephalopathic patients hospitalized during the years 1971-1973 presenting clinical symptoms similar to the above cited cases. The relative data are summarized in the following Table II.

Table II

| CONTROLS | | | |
|---|---|---|---|
| Age and sex | Neurologic clinical exam | | |
| | Entry | 5th day | Discharge |
| 80 F | R. Hemipl. | Unchanged | Aphasis, spastic phase. |
| 76 F | R. Hemipl. | Unchanged | Spastic phase. |
| 65 F | R. Hemipl. | Unchanged | R. Hemiparesis. |
| 79 M | R. Hemipl. aphasia | Hemipl. | Spastic phase. |
| 74 F | L. Hemipl. | Unchanged | Spastic phase. |
| 65 F | R. Hemipl. | Exitus | |
| 66 F | R. Hemipl. | Exitus | |
| 90 F | R. Hemipl. | Exitus | |
| 72 M | Hemiplaresis | R. Hemipl. | Cerebral coma; spontaneous discharge. |
| 76 F | L. Hemiparesis | Unchanged | Good autonomy |
| 73 F | L. Hemipl. | Exitus | |
| 72 F | R. Hemipl. | Exitus | |

A comparison of Tables I and II is clearly favorable to the use of Trazodone in acute cerebral syndromes. This clinical use is completely different from those previously known for Trazodone, which were for an essentially psycopharmacological type of utility.

EXAMPLE 2—Experimental and Clinical Report

It is generally recognized that the adverse sequelae of acute stroke not only depend on the extent of the ischemic area, but also on a more generalized involvement of the cerebral circulation with altered vascular permeability, edema and tissue compression. These latter phenomena have been correlated, on the basis of both experiemental and clinical data (1-3), with a local release or accumulation of serotonin, thus suggesting a potential interest of antiserotonin agents in acute stroke. In this connection, Trazodone presents some promising features. In fact, although primarily known as an antidepressant drug (4), Trazodone is a potent and selective antagonist of the peripheral effects of serotonin (5-6). Moreover, Trazodone reduces intraocular pressure both in laboratory animals (7-8) and in humans (9), thus suggesting to the inventor that a similar action might occur on cerebrospinal fluid (CSF) pressure.

In these experiments, Trazodone was investigated in rats in order to study its effects on CSF pressure and serotonin-induced paw edema. A pilot clinical study was also performed in patients with acute stroke due to thrombosis or embolism; patients with hemorrhagic conditions were not included in this trial because of the possible risk connected with a reduction in intracranial pressure.

The animal study was performed on Long Evans rats of both sexes, weighing 200-350 g.

CSF pressure was recorded under ether anaesthesia from the cisterna magna according to the method of Jeffers and Griffith Jr. (10).

In the various experimental groups CSF pressure was recorded both 10 min and immediately before treatments, and only rats showing constant values were used. The values of CSF pressure were around 70 mm $H_2O$. Body temperature was recorded with an electric thermometer inserted 3 cm into the rectum. The room temperature was 25° C. Trazodone was given i.v. at the volume 1 ml/kg in 10 sec. The controls and the treated rats were compared according to the covariance test.

Paw edema was produced in non-anaesthetized rats with a solution of serotonin (0.001%) or carrageenin (1%) injected into the plantar surface of the paw. The paw volume was measured according to the method of Lence (11). The edema was calculated as the different between the paw volume before and after injection of serotonin or carrageenin. Trazodone was given i.v. at the volume of 10 ml/kg in 10 sec; treatment was preformed at the same time as the injection of the irritating agents into the paw. Statistical significance of the results was assessed according to the Student's "t" test.

The clinical study was performed on a total of 45 patients who had been hospitalized for acute cerebral thrombosis or embolism. Table III gives the fundamental data pertinent to the patients under observation.

Table III

| SUMMARY OF DATA ON THE PATIENTS UNDER OBSERVATION | | | | |
|---|---|---|---|---|
| Experimental Group | No. of patients | Average age | Sex | Diagnosis |
| Trazodone therapy | 21 | 69 ± 1.3 | 17 M 4 F | 15 cerebral infarcts 3 subcortical temporal infarcts 2 brainstem infarcts 1 cerebellar infarct |
| Traditional therapies | 24 | 68 ± 2.1 | 11 M 13 F | 23 cerebral infarcts 1 subcortical temporal infarct |

21 of the patients were given Trazodone at the dose of 10 mg by slow i.v. injection, twice daily (morning and evening). The remaining 24 patients received a traditional therapy which included dexamethasone, mannitol and papaverine, and were used as controls; the choice of the drug and the dosage were not standardized, as they depended on the severity of the condition and its clinical course. Treatments commenced upon admission to hospital (which generally occurred within 2-3 hours from the beginning of the attack) and were continued for 7 days.

The assessment of the neurological condition was made according to the scoring system by Patten et al. (12), taking into consideration orientation, recent recall, motor function and aphasia, upon admission; on the 3rd and 5th day of hospitalization and again on the day of discharge. In order to facilitate the elaboration of the data, evaluation of orientation was made on a maximum score of 5 instead of 6. The other parameters taken into consideration were the duration of hospitalization, as the patients were discharged as soon as the clinical condition improved and appeared to be stabilized as well as deaths within the first 35 days. The average blood pressure upon admission was 90-180 mm Hg and average pulse rate 91. These parameters were similar in both experimental groups at the readings made on the 3rd and 5th day of hospitalization and on the day of discharge and, therefore, will no longer be referred to.

Statistical analysis of the results was made according to the covariance of Chi-Square test.

RESULTS

FIG. 1 illustrates the effects of Trazodone on CSF pressure in rats; these are given by making the control CSF pressure values equal to 100.

CSF pressure was reduced at dose of 0.03 and 0.01 mg/kg i.v., although only the latter effect was statistically significant.

The Trazodone treatment did not influence the body temperature of rats in the above experiment.

The results of the experiements conducted on serotonin-induced paw edema in rats are summarized in Table IV.

Table IV

Effects of a single i.v. injection of Trazodone on serotonin-induced paw edema in rats. Results are given by making the control values equal to 100.

| Dose mg/kg | no. of rats treated | Controls | Time in hours and % inhibition of edema | | | |
|---|---|---|---|---|---|---|
| | | | 1 | 2 | 4 | 6 |
| 0.1 | 22 | 22 | 0 | 7 | 18 | 19 |
| 0.15 | 13 | 13 | 30[b] | 26 | 36 | 62 |
| 0.3 | 16 | 16 | 47[a] | 60[a] | 91[a] | 100[a] |

[a] $p < 0.001$;
[b] $p < 0.02$

The minimal effective dose of Trazodone in this test was 0.15 mg/kg i.v. which produced a short-lasting effect; at the dose of 0.3 mg/kg i.v. the effect was stronger and longer lasting.

On carrageenin-induced paw edema Trazodone had no action at the dose of 0.3 mg/kg i.v.; this experiment was conducted on a total of 28 rats, 13 of which were used as controls.

FIG. 2 gives the average total score of disability in the clinical patients treated with Trazodone and in the control group, calculated on the following items: orientation, recent recall, motor function and aphasia.

As can be seen from FIG. 2 the initial score was slightly higher in the group treated with Trazodone than in the control group, but the difference was not statistically significant. At all the subsequent readings the patients treated with Trazodone had a lower score than the control group and the difference was statistically significant.

FIG. 3 reports the percentage of patients discharged at various times. In the group treated with Trazodone the percentage of patients discharged was signficicantly higher as from day 21.

The average hospitalization period was 15.6 days for the group treated with Trazodone and 25.9 days fro the controls. The difference was shown to be significant with the Student's "t" test ($P < 0.01$). The mortality rate was 19% in the Trazodone group and 33% in the control group. There was no statistically significant difference with the Chi-Square test.

DISCUSSION

The results of these experiments confirm that Trazodone has a selective action on some tissue responses to serotonin; in fact, Trazodone inhibited serotonin-induced paw edema. Moreover, it was observed that Trazodone lowers the CSF pressure in rats under ether anaesthesia; since ether and other volatile anasthetics are known to increase CSF pressure (13,14). It is still to be stablished whether or not Trazodone is also effective in normal animals.

Even if these data are only an indirect evidence of the potential interest of Trazodone in acute stroke, the clinical trial appeared to be justified for different reasons. First of all, a trial with Trazodone was in agreement with the basic data already mentioned, suggesting a role of serotonin in the sequelae of cerebral infarction. Secondly, Trazodone is a well tolerated drug (15,16) and animal data suggested that it might be effective at much lower doses than those already used in psychiatric conditions (17). Thirdly, stroke is a serious condition for which no universally accepted treatments have been found so far; even corticosteroid therapy which in some cases has shown statistically significant effects (12), in others, has been reported to have no effect (18).

Trazodone in patients with acute stroke proved to have a favourable influence on the following items: orientation, recent recall, motor function, aphasia.

Duration of hospitalization was also shorter in the Trazodone patients; since patients were discharged when their clinical condition was improved, the latter result is a further indication of Trazodone's efficacy in acute stroke.

The results of these tests should be considered preliminary on account of the small number of patients, in consideration of the experimental conditions used, the study was not blind and treatment of the control patients was not standardized as the choice of the drugs and their doses depended on the severity and clinical course of the condition. These results show the utility of Trazodone in acute stroke.

REFERENCES:

1. Bell, W. H., Sundt, T. M. Jr. and Nofzinger, J. D.; The response of cortical vessels to serotonin in experimental cerebral infarction, J. Neurosug. 26: 203-212, 1967.
2. Costa, J. L., Ito, U., Spatz, M., Klatzo, I. and Demirjian, C.: 5-Hydroxytrptamine accumulation in cerebro-vascular injury. Nature (Lond.), 248: 135-136, 1974.
3. Meyer, J. S. and Welch, K. M. A.: Contribution of platelet aggregation and serotonin release to progressive cerebral infarction. Abstracts of the Round Table discussion "Platelets aggregation in the pathogenesis of cerebrovascular disorders"—Roma, October 1974, (I Clinica delle Malattie Nervose e Mentali, Universita degli Studi di Roma).
4. Ban, Th. A. and Silverstrini, B.: "Trazodone", Mod. Probl. Pharmacopsychiat., 9, S. Karger, Basel, 1974.
5. Silvestrini, B., Cioli, V., Burberi, S. and Catanese, B.: Pharmacological properties of AF 1161, a new psychotropic drug. Int. J. Neuropharmacol., 7: 587–599, 1968.
6. Boissier, J. R., Portmann-Cristesco, E., Soubrie, P. and Fichelle, J.: Pharmacological and biochemical features of trazodone. In: "Trazodone"—Eds: Th. A. Ban and B. Silvestrini, Mod. Probl. Pharmacopsychiat., 9: 19–28, S. Krager, Basel, 1974.
7. Burberi, P., Piccinelli, D. and Silvestrini, B.: Effects of sistemically administered drugs on intraocular pressure in rabbits. Arzneimittel-Forscg., 20: 1143–1147, 1970.
8. de Feo, G., Piccinelli, D., Putzolu, S. and Silvestrini, B.: Effects of topically instilled drugs on intraocular pressure in rabbits. Arzneimittel-Forsch., 25: 806–809, 1975.
9. Daniele, S. e Fiore, C.: Effetto ipotensivo oculare del-l'AF 1161 (Trazodone). Ann. Ottal., 98: 1–6, 1972.
10. Jeffers, W. A. and Griffith, J. Q., Jr.: The central nervous system. In: "The rat in laboratiry investigation"Eds; E. J. E. Farris and J. Q. Griffith, Jr.—2nd Edition, 196–202, J. B. Lippincott Co., Philadelphia, 1949.
11. Lence, P.: A new device for plethysmoscopic measuring of small objects. Arch. int. Pharmacodyn, 136: 327–241, 1962.
12. Patten, B. M., Mendell, J., Bruun, B., Curtin, W. and Carter, S.: Double-blind study of the effects of dexamethasone on acute stroke. Neurology (Minneap.), 22: 377–383, 1972.
13. Davson, H. "Physiology of the cerebrospinal fluid". p. 358, J. & A. Churchill, London, 1970.
14. Carpi, A.: Pharmacology of the cerebral circulation. In: "International Encyclopedia of Pharmacology and Therapeutics" Section 33: 1, p. 155, Pergamon Press, Oxford, 1972.
15. Ucha Udabe, R.: Clinical experience with a new psychotropic drug, Trazodone (a review of literature). Curr. ther. Res., 15: 755–763, 1973.
16. Rivett, K. F. and Scorza Barcellona, P.: Toxicology of trazodone. In: "Trazodone"—Eds: Th. A. Ban and B. Silvestrini, Mod. Probl. Pharmacopsychiat., 9: 76–86, S. Karger, Basel, 1974.
17. Pariante, F.: Clinical effect of intravenous trazodone administration in severe depression. In: "Trazodone'-'—Eds. Th. A. Ban and B. Silvestrini, Mod. Probl. Pharmacopsychiat, 9: 176–181, S. Karger, Basel, 1974.
18. Paulson, O. B.: Cerebral apoplexy (Stroke): pathogenesis, pathophysiology and therapy as illustrated by regional blood flow measurements in the brain. Stroke, 2: 327–360, 1971.

While the trials of the Examples have been conducted with Trazodone, the preferred compound, other compounds within the scope of U.S. Pat. No. 3,381,009 will also serve in varying degrees based upon their interference with the serotoninergic systems involved in the stroke syndrome.

It is preferred to administer the active materials by slow intravenous injection from buffered saline solutions.

Trazodone for injection is prepared in ampules, each containing 25 mgm of Trazodone and 18.75 mgm of NaCl dissolved in water for injection q.s. to provide 2.5 mgm Trazodone/cc of final solution. In adults presenting the stroke symptoms a dose of 10 mgm, by slow injection, twice daily is adequate. However, the dosage should be adjusted based upon body weight of the patient and the severity of the clinical picture.

After stabilization of the clinical improvements, administration by the oral route can be used with selected patients. Syrups and tablet can be used when patients present no swallowing problems. The usual pharmaceutically acceptable vehicles can be used. Rectal instillation from suppositry bases can be effective for patients with swallowing difficulties resulting from the stroke.

The above examples are illustrative of the invention in its most preferred modes but do no preclude the use of art-recognized alternatives, and equivalents.

I claim:

1. A method for treating individuals suffering from the acute phases of the organic cerebral syndrome due to arterial occlusion which comprises administering to such individual patients effective amounts of 2-[3-(4-m-chloro-phenyl)-1-piperazinyl]-propyl-s-triazolo [4,3a]-pyridin-3(2H) one and the non-toxic salts thereof with organic or inorganic acid in a pharmaceutically acceptable vehicle.

* * * * *